United States Patent [19]
Kundu et al.

[11] Patent Number: 5,854,076
[45] Date of Patent: Dec. 29, 1998

[54] METHOD FOR TESTING COAGULATION OF BLOOD THROUGH BIOACTIVE POROUS PARTITION MEMBERS

[75] Inventors: Sourav K. Kundu, Cooper City, Fla.; Ted S. Geiselman, Bolton, Mass.

[73] Assignee: Dade International Inc., Deerfield, Ill.

[21] Appl. No.: 660,771

[22] Filed: Jun. 6, 1996

Related U.S. Application Data

[60] Continuation of Ser. No. 450,936, May 23, 1995, abandoned, which is a division of Ser. No. 269,185, Jun. 30, 1994, abandoned.

[51] Int. Cl.⁶ .................................................. G01N 33/86
[52] U.S. Cl. .................................. 436/69; 436/70; 422/58; 422/61; 422/73; 422/82.05; 422/101; 422/102
[58] Field of Search ........................... 422/56–58, 61, 422/73, 82.05, 101, 102; 436/69, 70, 158, 159; 73/64.41

[56] References Cited

U.S. PATENT DOCUMENTS

| | | | |
|---|---|---|---|
| 2,616,796 | 11/1952 | Schilling et al. | 436/69 |
| 3,219,421 | 11/1965 | Schwarz, Jr. et al. | 436/69 |
| 3,267,362 | 8/1966 | Page | 324/30 |
| 3,267,364 | 8/1966 | Page et al. | 324/30 |
| 3,268,804 | 8/1966 | Young | 436/69 |

(List continued on next page.)

FOREIGN PATENT DOCUMENTS

| | | |
|---|---|---|
| 2096329 | 9/1985 | United Kingdom . |

OTHER PUBLICATIONS

"Platelet Function Analyzer PFA–100", Baxter.
G. Dietrich et al., *Infusionstherapie*, 17:214–216 (1990), "Primary Hemostatis in Hemodilution –2) Infusion Solutions".
G. Dietrich et al., *Lab. Med.*, 17:317 (1993), "The In Vitro Bleeding Test Standardization Of The Methodical Procedure".
M.A.A. Kratzer et al., *Haemostasis*, 15:363–370 (1985), "Detection Of Abnormal Platelet Functions With An In Vitro Model Of Primary Haemostasis".
M.A.A. Kratzer et al., *Haemostasis*, 15:357–362 (1985), "Simulation Of Primary Haemostasis In Vitro".
V. Kretschmer et al., *Transfus. Sci.*, 14:27–34 (1993), "Determination of Bleeding Risk in Thrombocytopenic Patients Receiving Platelet Substitution".
V. Kretschmer et al., *Blut*, 59:188 (1989), "In Vitro Bleeding Test—A Sensitive Method For The Detection Of Platelet Function Impairment And A Potential Test For The Control Of Low–Dose Aspirin Efficacy".
V. Kretschmer et al., *Thrombosis Research*, 56:593–602 (1989), "In Vitro Bleeding Test—A Simple Method For The Detection Of Aspirin Effects On Platelet Function".
K.J. Eriksson et al., *Eur. J. Haematol.*, 51,152–155 (1993), "Functional Capacity Of Transfused Platelets Estimated By The Thrombostat 4000/2".
N. Maurin, *The International Journal Of Artifical Organs*, vol. 11, No. 4, (1988), "The in vitro Bleeding Time While Using A Stable Prostacyclin Analogue During Hemodialysis".
T. Tsujinara et al., *Japanese Journal Of Surgery*, vol. 18, No. 1, pps. 430–437, (1988), "Clinical Application Of A New in vitro Bleeding Time Device On Surgical Patients".
R. Alshameeri et al., *Thromb. Haemost* 1993, 69:1146, "Evalution Of An In Vitro Bleeding Time Device, Thrombostat 4000".

*Primary Examiner*—Harold Y. Pyon
*Attorney, Agent, or Firm*—Cara Z Lowen; Linda M Buckley

[57] ABSTRACT

The present invention provides methods of using bioactive porous partition members for testing the blood coagulation process or platelet function, wherein the porous partition members have an aperture and have incorporated therein at least one agent capable of initiating blood coagulation or platelet aggregation.

8 Claims, 2 Drawing Sheets

U.S. PATENT DOCUMENTS

| | | | |
|---|---|---|---|
| 3,539,300 | 11/1970 | Stone | 422/73 |
| 3,605,010 | 9/1971 | Folus | 324/30 R |
| 3,694,161 | 9/1972 | Kleszynski et al. | 23/230 B |
| 3,914,985 | 10/1975 | von Behrens | 73/64.1 |
| 3,918,908 | 11/1975 | Moyer et al. | 23/230 B |
| 4,451,568 | 5/1984 | Schneider et al. | 435/181 |
| 4,458,678 | 7/1984 | Yannas et al. | 602/48 |
| 4,533,519 | 8/1985 | Baugh et al. | 422/73 |
| 4,534,939 | 8/1985 | Smith et al. | 422/61 |
| 4,599,219 | 7/1986 | Cooper et al. | 422/61 |
| 4,604,894 | 8/1986 | Kratzer et al. | 73/64.1 |
| 4,752,449 | 6/1988 | Jackson et al. | 422/73 |
| 4,777,141 | 10/1988 | Calzi et al. | 436/69 |
| 4,780,418 | 10/1988 | Kratzer | 436/69 |
| 4,784,944 | 11/1988 | Kolde | 435/13 |
| 4,788,139 | 11/1988 | Ryan | 435/13 |
| 4,812,293 | 3/1989 | McLaurin et al. | 422/69 |
| 4,865,813 | 9/1989 | Leon | 422/101 |
| 4,983,514 | 1/1991 | Weithmann et al. | 435/29 |
| 5,047,211 | 9/1991 | Sloane, Jr. et al. | 422/73 |
| 5,051,239 | 9/1991 | von der Goltz | 422/73 |
| 5,089,422 | 2/1992 | Brubaker | 436/69 |
| 5,091,304 | 2/1992 | La Duca et al. | 435/13 |
| 5,093,237 | 3/1992 | Enomoto | 435/13 |
| 5,139,944 | 8/1992 | Sawyer et al. | 435/226 |
| 5,174,961 | 12/1992 | Smith | 422/73 |
| 5,187,102 | 2/1993 | Stocker et al. | 436/69 |
| 5,196,403 | 3/1993 | Maraganove et al. | 514/12 |
| 5,221,614 | 6/1993 | Enomoto | 435/13 |
| 5,223,227 | 6/1993 | Zuckerman | 422/102 |
| 5,246,666 | 9/1993 | Vogler et al. | 422/73 |
| 5,246,715 | 9/1993 | Orevi et al. | 424/550 |
| 5,275,953 | 1/1994 | Bull | 436/69 |
| 5,281,661 | 1/1994 | Linnau et al. | 525/54.1 |
| 5,314,826 | 5/1994 | Baugh | 436/69 |
| 5,316,730 | 5/1994 | Blake et al. | 422/73 |
| 5,339,830 | 8/1994 | Blake, III | 128/771 |
| 5,569,590 | 10/1996 | Speck | 435/13 |
| 5,602,037 | 2/1997 | Ostgaard et al. | 436/69 |

5,854,076

METHOD FOR TESTING COAGULATION OF BLOOD THROUGH BIOACTIVE POROUS PARTITION MEMBERS

This application is a continuation of application Ser. No. 08/450,936 filed on May 23, 1995, now abandoned which is a divisional of U.S. Ser. No. 08/269,185 filed on Jun. 30, 1994, now abandoned.

BACKGROUND OF THE INVENTION

The present invention provides bioactive porous partition members for use in connection with studies or tests of the blood coagulation process.

Hemostasis or stoppage of bleeding involves the interplay of two biochemical pathways which are controlled by various protein factors. The processes by which blood coagulates as it is presently understood involve a multi-step cascade of activations of the protein factors that culminate in fibrin formation. Various tests have been developed to test the individual steps of this cascade in order to determine whether the blood of a patient can properly clot or whether there is clotting disorder in which there is a deficiency of one or more of the factors necessary for proper clotting. It is well known that the condition of the platelets or the platelet function of blood is one indication of the ability of blood to properly clot.

Coagulation of blood is a multi-step cascade of activations of protein factors that culminate in fibrin formation. There are two pathways of activation, an intrinsic pathway involving only blood factors and an extrinsic pathway that is believed to require the participation of a tissue lipoprotein (tissue factor). The operation of both seems to be necessary for effective hemostasis; deficiencies of factors in either can result in a hemorrhagic state.

Tests have been developed to measure these pathways. The prothrombin time (PT) test measures the extrinsic pathway. The partial thromboplastin time (PTT) test measures the intrinsic pathway. These tests are routinely performed on patients going into surgery.

Methods in use for testing platelet functions include the platelet adhesion test, platelet aggregation test and the bleeding time test.

The bleeding time test is the primary existing test in use for testing platelet function or Primary Hemostasis on whole human blood.

U.S. Pat. Nos. 4,604,894; 4,780,418; and 5,051,239 disclose assay systems which can be used to perform an in vitro test on blood that can be accurately and reproducibly correlated to the in vivo bleeding time test described above, thereby eliminating involvement of the patient. The Thrombostat™ 4000 system, in current use, is one such system. Platelet function is evaluated in these systems by aspirating anticoagulated whole blood samples at a constant negative pressure through a small aperture positioned at the center of a separating wall which may be non-porous or porous. In systems wherein the separating wall is porous, it is wetted prior to the start of the assay with an activator that activates coagulation of blood platelets. A platelet plug forms at the aperture and the time required for the cessation of blood flow to occur is determined. This time is then correlated to platelet function, i.e., in vivo bleeding time.

The Thrombostat™ 4000 system is not in widespread use, due largely to the present configuration which is costly and does not lend itself to automation for a number of reasons, including limitations of the device which holds the sample to be tested. The device currently used with the Thrombostat™ 4000 consists of three separate parts: a reagent/test chamber, a capillary, and a sample cup. A porous separating wall containing collagen is disposed in the reagent/test chamber. The reagent/test chamber then must be stored in a separate hermetic package apart from the capillary and sample cup to maintain stability of the collagen for the specified shelf life. The capillary and reagent/test chamber must be manually assembled by the operator at the start of each test being performed. Furthermore, the sample to be tested must be pipetted into the sample cup and incubated before the sample cup can be assembled to the capillary and reagent/test chamber. In addition, the incubation step is manually timed by the operator. The separate incubation step requires additional handling after the incubation period, when the operator manually places the assembled capillary and reagent/test chamber into the sample cup and initiates the testing sequence. At the end of the test, the capillary is removed and cleaned for reuse because of its high cost.

Test cartridges specifically adapted for use in an assay for testing a coagulation function of blood such as the measurement of platelet function, including but not limited to automated versions of those assays described in U.S. Pat. Nos. 4,604,894, 4,780,418, and 5,051,239 discussed above have been developed and are disclosed in copending U.S. patent application Ser. No. 08/269,184, filed Jun. 30, 1994. One such test cartridge ("Test Cartridge") comprises a housing, wherein the housing comprises:

(a) a holding chamber for receiving a sample of the blood to be tested and a test chamber, wherein the holding chamber and test chamber are separated by a pierceable member;

(b) a partition member disposed in the test chamber, the partition member having an opening therethrough and comprising at least one reagent which activates at least one pathway of the coagulation of blood;

(c) a transfer member movably mounted in the test chamber so that it can be moved towards and pierce the pierceable member; and (d) a receiving chamber disposed in the test chamber between the partition member and the transfer member for receiving blood from the transfer member.

In use, blood is disposed by a user in the holding chamber and the test cartridge is placed in an instrument for incubation. After incubation, the transfer member is moved towards and pierces the pierceable member to contact the blood and a negative pressure is created in the test chamber, blood moves through the transfer member into the receiving chamber and through the opening in the partition member.

These Test Cartridges are intended for use with an instrument which automates some or all of the steps of the assay being conducted.

The design and geometry of the housing of the Test Cartridges and its components is selected based on the assay to be performed. In one embodiment, the test chamber is adapted to receive a sample cup, the sample cup having disposed therein the partition member, the receiving chamber and the transfer member. In such embodiments, the assay takes place in the vicinity of the partition member, the liquid sample being aspirated from the holding chamber through the transfer member into the receiving chamber positioned just below the partition member, and through the opening in the partition member.

The partition member may be porous and wetted with reagents or it may be in the form of a non-porous plate. In embodiments adapted for testing a coagulation function of blood, the partition member typically comprises a porous member which is provided with at least one reagent involved in the coagulation of blood. In one Test Cartridge specifically adapted for testing platelet function, the blood entry side of the partition member comprises a collagen material as disclosed in U.S. Pat. Nos. 4,604,894 and 5,051,239 which acts as an activator for platelet function. Also as disclosed, adenosine 5'-diphosphate (ADP) can, if desired, be supplied to the porous member before use. It is supplied before use, because ADP is known to be unstable in aqueous solutions, having a useful life of only about 4 hours.

The Test Cartridges are useful in testing blood coagulation generally, as well as specifically as blood coagulation is affected by various agents which may be present in a patient's blood or by factors which are lacking or impaired and so forth. The Test Cartridges adapted for use in the platelet function test are useful, for example, presurgically to predict risk of bleeding, in blood banks for donor screening for functional platelets and quality control tests for platelet function prior to administration, and in hospitals in post administration testing to determine how a patient is responding to platelet infusion, and so forth.

It can be seen that both the Thrombostat™ 4000 system and the Test Cartridge could be improved if necessary reagents for the test, such as ADP, could be provided to a user incorporated in the porous partition member, thereby improving reproducibly and efficiency by eliminating the need for a user to prepare reagents and add them to the device during a test.

SUMMARY OF THE INVENTION

Figure 1:
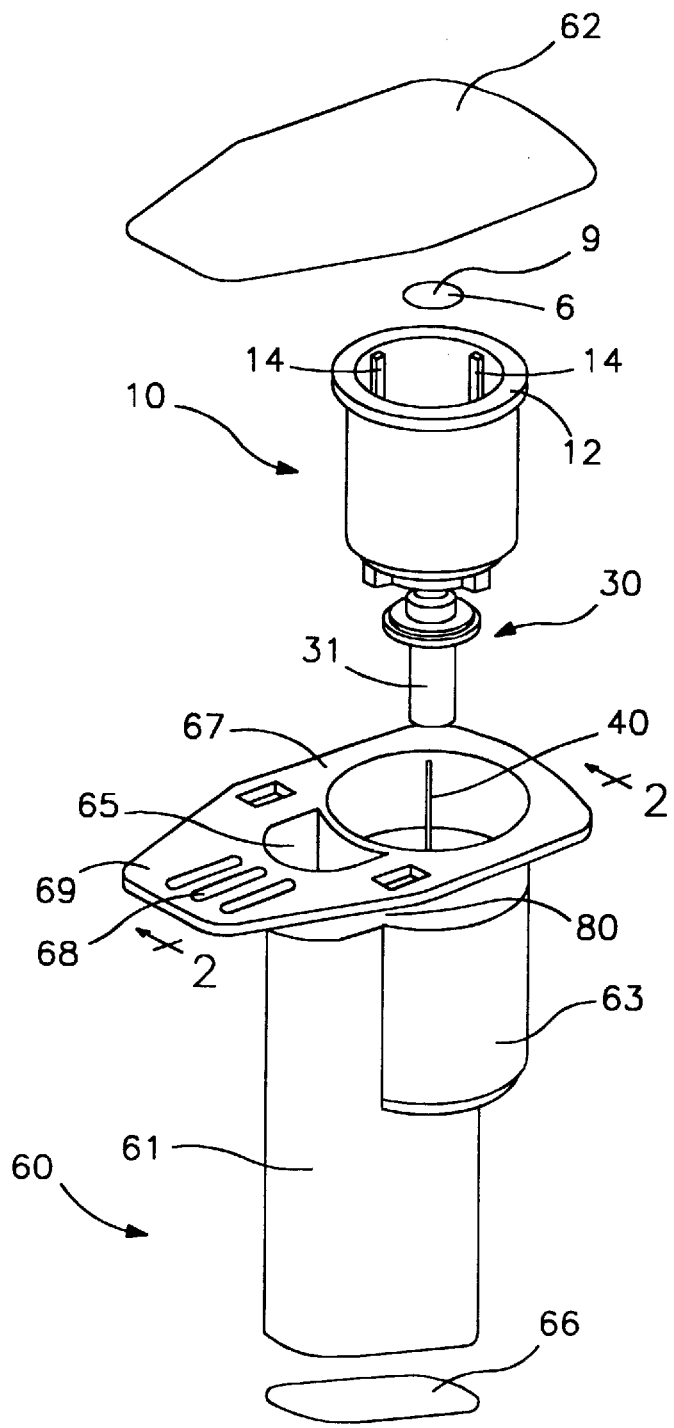
FIG. 1 is an exploded isometric view of components of a Test Cartridge incorporating a porous partition member in accordance with the present invention.

The present invention provides bioactive porous partition members useful in assay systems for testing a coagulation function of blood, including platelet aggregation. These porous partition members are useful in the evaluation of two main components of the hemostatic mechanism, namely, coagulation and platelet function on anticoagulated whole blood samples.

The porous partition members of the present invention have incorporated therein one or more agents capable of initiating the coagulation process in anticoagulated whole blood and blood plasma or initiating platelet aggregation in anticoagulated whole blood and platelet rich plasma. It has unexpectedly been discovered that these agents can be incorporated into these porous partition members, dried and then reconstituted at the time of the assay.

The porous partition members of the present invention are useful in assay systems for testing a coagulation function of blood, such as those systems disclosed in U.S. Pat. Nos. 4,604,894; 4,780,418; and 5,051,239. It is believed that they could also replace the membrane disclosed in U.S. Pat. No. 5,089,422. These porous partition members are particularly useful in the Thrombostat™ 4000 and Test Cartridges as described above.

The agent or agents incorporated in the porous partition members of the present invention are selected based upon the particular coagulation function of blood being evaluated.

In assay systems for testing platelet function, platelet aggregation modulation agents, such as ADP, are incorporated into the porous partition members of the present invention. The present invention also provides porous partition members having incorporated therein other standard modulating agents, such as ristocetin, arachidonic acid and salts thereof, thrombin, epinephrine, platelet activating factor (PAF), thrombin receptor agonist peptide (TRAP), and so forth which are useful in the evaluation of various aspects of platelet function.

The porous partition members of the present invention are also useful in whole blood and blood plasma coagulation assays to evaluate coagulation functions, similar to PT and PTT tests. In such embodiments, clot formation is initiated by blood contact with appropriate activators of extrinsic or intrinsic pathways which have incorporated in the porous partition member which ultimately causes cessation of blood flow through the porous partition member. The time required for cessation of blood flow to occur can be correlated, e.g., to the prothrombin time or the partial thromboplastin time for the patient. In contrast, present whole blood coagulation instruments rely on changes in optical signals or electrical signals upon formation of a clot.

Activators of the extrinsic pathway of prothrombin conversion suitable for incorporation in the porous partition members of the present invention include thromboplastin reagents, e.g., THROMBOPLASTIN-C®, Baxter-Dade. Activators of the intrinsic pathway suitable for incorporation in the porous partition members of the present invention include inosithin, and calcium chloride and/or activated cephaloplastin reagent (ACTIN®, Baxter-Dade). ACTIN® may be incorporated in the porous partition member or premixed with a whole blood sample to be tested. These tests can be carried out both on anticoagulated whole blood and on plasma samples.

The concentration of agent or agents in the porous partition member are selected so as to result in an aperture closure time which shows a difference between normal and abnormal coagulation parameters.

In the platelet function test, adenosine 5' diphosphate (ADP) is a preferred reagent for incorporation in the porous partition members of the invention. ADP is unstable in aqueous solution having a useful life of only about 4 hours. It was unexpectedly found that by incorporating ADP in a porous partition member, drying it and storing it at about 4° C. under hermetically sealed conditions, it is stable for about one and one-half years. By eliminating the need for a user to prepare ADP solutions for use in the assay, such porous partition members eliminate user error, permeation variability, and provide reproducible stimulation for platelet aggregation.

In another preferred embodiment of a porous partition member for use in testing platelet function, in addition to the incorporation of ADP therein, a collagen coating is also provided on the porous partition member as disclosed in U.S. Pat. Nos. 4,604,894 and 5,051,239. In one preferred embodiment of the present invention, the porous partition member is porous to saline, since saline is a preferred wetting solution which can be dispensed onto the membrane to bring the ADP back into the solution during an assay.

In another preferred embodiment for testing platelet function, epinephrine is incorporated in a porous partition member in accordance with the present invention. Epinephrine is sensitive to aspirin induced defects in platelets. Like ADP, epinephrine is unstable in solution but has been found to have good stability when incorporated in a porous partition member of the present invention and dried.

Porous partition members for use in the present invention provide a support matrix for the for the agent or agents which promote the clotting or coagulation of blood. The preferred partition material has absorbency to liquids so that reagents can be incorporated therein, yet has a stable structure so that a precise opening can be, for example, punched therein. One preferred porous partition member comprises a membrane.

Membranes are generally useful in the practice of this invention. The agents to be incorporated in the membrane must be able to penetrate the membrane and, in some embodiments saturate the membrane thereby, forming a film on the membrane as well as being incorporated therein.

Preferred partition members for use in the present invention include cellulose esters, ceramic, nylon, polypropylene, polyvinylidene fluoride (PVDF), and fiberglass. A particularly preferred porous partition member is a mixed cellulose ester (acetate and nitrate) membrane from Millipore.

The pore size in preferred membranes is such that agents can penetrate the membrane and there is no interference with creating a negative pressure, e.g., in the Test Cartridge, in order to aspirate blood through the aperture in the membrane. The pore size is also selected so that whole blood does not substantially penetrate the membrane but rather goes through the aperture in the membrane.

The porous partition member is able to maintain the size of the aperture therein, even when wet. It is also relatively inert to the agents used in the test and does not cause interfering activation of platelets or of the pathways. It is also temperature insensitive at the temperature of the test, e.g., 38° C.

The porous partition members of the present invention having incorporated therein, agents which allow direct and complete evaluation of platelet function and coagulation factors of blood provide easier, more reliable assay systems for testing a coagulation function of blood than those currently available with different agonists in platelet aggregometry.

DESCRIPTION OF THE INVENTION

One Test Cartridge specifically adapted for use in an instrument which is capable of carrying out an automated version of those assays for testing platelet function disclosed in U.S. Pat. Nos. 4,604,894, 4,780,418, and 5,051,239 is shown in cross-section in FIG. 1. The porous partition members of the present invention are particularly useful in such Test Cartridges. These assays involve an incubation step in the instrument during which the liquid sample of blood to be analyzed and components of the assay are heated to a particular temperature and during this incubation step the sample and assay components are kept separated.

After the incubation step, the instrument causes the transfer member to pierce the pierceable section between the holding and test chambers and to move into contact with the blood, and causes blood to be aspirated through the transfer member and the porous partition member by creating a negative pressure in the housing as will be more fully discussed hereinafter.

Figure 2:
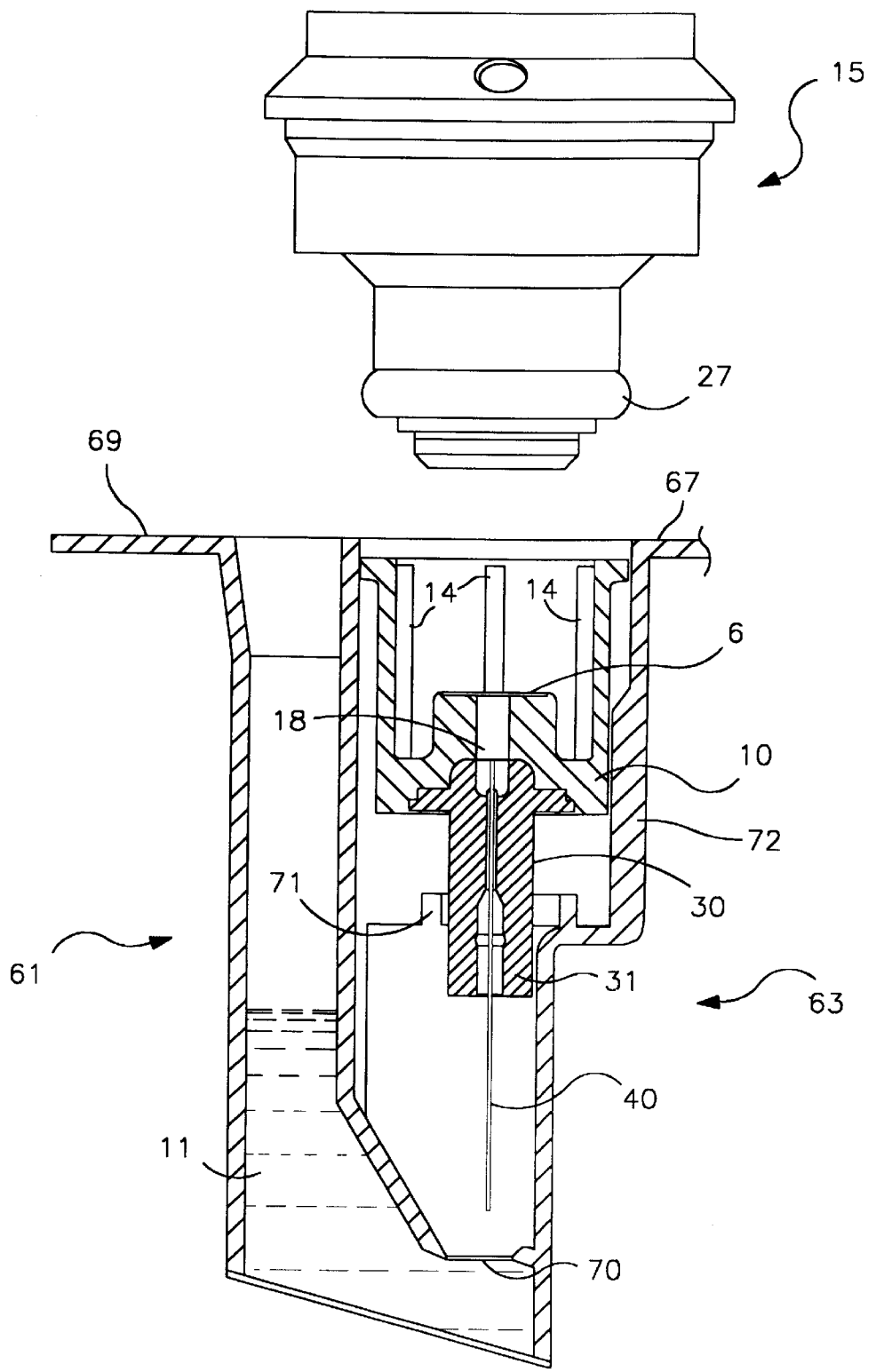
FIG. 2 is a cross section taken along line 2—2 of FIG. 1 wherein the Test Cartridge shown in FIG. 1 is shown in assembled form and further shows a portion of an instrument for use with the Test Cartridge.

FIG. 1 shows an isometric, exploded view of one Test Cartridge which incorporates a porous partition member 6 having aperture 9 in accordance with the present invention. A cross section of the device along line 2—2 of FIG. 1 in assembled form and containing sample 11 is shown in FIG. 2, which also shows a component of one instrument which can be used with the devices of the present invention.

Referring now to FIG. 1, porous partition member 6 is provided with aperture 9.

The Test Cartridge shown in FIG. 1 comprises a housing 60 which defines holding chamber 61 and test chamber 63. Housing 60 is provided with flange 67 and tab 69.

Housing 60 is provided with a removable top seal 62 which in the assembled device is hermetically sealed to flange 67 and closed at the bottom with bottom seal 66.

Test chamber 63 is adapted to receive sample cup 10. Sample cup 10 supports a reagent treated porous partition member 6 of the present invention having aperture 9 therein and a capillary hub 30 which provides a mechanism to operably attach capillary 40 to sample cup 10. The interior of sample cup 10 is provided with four vacuum chuck stop ribs 14 for positioning, two of which are shown in FIG. 1.

Housing 60 is adapted to mate with an instrument which can create a negative pressure in test chamber 63 or in a part of test chamber 63. In the embodiment shown, this is accomplished by rim 12 of sample cup 10 which comprises a part of test chamber 63. The instrument has a mating component which is capable of sealably mating with rim 12 of sample cup 10. In the embodiment shown in FIGS. 2 to 4, the mating component comprises vacuum chuck 15 shown. Vacuum chuck 15 is provided with O-ring 27 which during the assay sealably meets rim 12. Vacuum chuck 15 is moved by the instrument to contact rim 12 and to exert a downward pressure on sample cup 10 to move transfer member 40 towards pierceable member 70, causing it to pierce the pierceable member and extend into sample 11 in the holding chamber. Vacuum chuck stop ribs 14 in sample cup 10 limit the downward movement of vacuum chuck 15.

When the porous partition member of the present invention is used in a Test Cartridge such as that shown in the Figures, sample is caused to flow from holding chamber 61 to test chamber 63 by the negative pressure created by the instrument.

Opening 9 in partition member 6 is dimensioned so that under the conditions of the particular assay a plug will be formed and the opening closed. If the aperture is too small non-assay related blockages will occur. If it is too big then a plug will not form properly. For the platelet function test, the aperture is preferably between about 100 microns to about 200 microns, more preferably about 140 microns to 160 microns, most preferably about 150 microns. The dimension of the aperture in partition member does not have a great influence on the initial flow characteristics in the device.

The porous partition members of the present invention are absorbent to liquids so that agents capable of initiating the blood coagulation process or platelet aggregation in blood can be incorporated therein, yet have a stable structure so that a precise opening can be, for example, punched. The porous partition members of the present invention also serve as a support matrix for collagen when collagen is used.

In the platelet function test, adenosine 5' diphosphate (ADP) is a preferred reagent for incorporating in the porous partition member. In embodiments, wherein the porous partition member is also provided with a collagen coating, a uniform layer of collagen around the aperture is highly desirable. The amount of collagen on the membrane is not particularly critical. A range of about 1–2 $\mu$g has been found to perform well in the platelet function assay.

The aperture closure time with a normal blood sample depends in part upon the concentration of the biologically active substance incorporated in the membrane. The concentration of agents is selected so as to provide a convenient distinction between normal and abnormal coagulation parameter. This can be readily determined by one of ordinary skill in the art. The concentration ranges of similar reagents reported for use in aggregometry provide one starting point in determining the appropriate concentration range. Reagent concentrations are optimized keeping in mind the desired sensitivity of the assay. For example, it is desirable that the concentration of ADP be sufficient to detect mild platelet dysfunction, but not so low as to introduce variable results.

A threshold amount is needed for complete activation and aggregation and if mild platelet disfunction is being studied, then a smaller amount of reagent is used. It can be seen that a balance between the sensitivity of the test and obtaining reproducible results is desired.

In one preferred embodiment of the present invention, lyophilized ADP or epinephrine bitartrate was dissolved in a sodium acetate-acetic acid buffer (pH 3.5) containing 5% glucose (osmolality 280 mOsm/kg). The concentration of ADP solution used for incorporation into the membrane was 50 mg/ml, and that of the epinephrine solution was 10 mg/ml.

A strip of membrane was spot-coated with 1 $\mu$L of ADP or epinephrine solution. Therefore, each membrane placed in the Test Cartridge contained 50 $\mu$g of ADP or 10 $\mu$g of epinephrine. The membrane was then spot-coated with 1 $\mu$L of fibrillar Type I collagen suspension from horse tendon available from Nycomed AG.

Spot-coating involved putting spots of liquid agent on a strip of membrane. After spot-coating, the membrane was placed in a forced air drying chamber for 25 minutes for drying of the ADP or epinephrine, and formation of a collagen film on the coated areas. Once dried, an aperture was punched in the center of the spot and a membrane disk was cut from the membrane strip. The membrane disk was inserted in a Test Cartridge similar to that shown in the Figures.

Prior to a blood test, saline was dispensed onto the membrane to bring the ADP or epinephrine into solution. However, it has been found that the test progressed normally, even without saline dispensed onto the membrane. The blood sample alone can dissolve the dried ADP or epinephrine present in the membrane.

For both tests, blood was aspirated through the aperture at a constant pressure gradient of about 40 mbar, and the time required for cessation of blood flow to occur was determined.

Activators of the extrinsic pathway of prothrombin conversion, such as thromboplastin reagents, can be incorporated in the porous partition member of the present invention. Activators of the intrinsic pathway, such as calcium chloride and cephaloplastin reagent can be incorporated in the porous partition members of the present invention.

The present invention has been described in detail, including the preferred embodiments thereof. However, it will be appreciated that those skilled in the art, upon consideration of the present disclosure, may make modifications and/or improvements of this invention and still be within the scope and spirit of this invention as set forth in the following claims.

What is claimed is:

1. A method of testing a coagulation function of blood which comprises passing blood through a device comprising a porous partition member, wherein the porous partition member has an opening and has dried therein at least one agent capable of initiating the blood coagulation process, wherein the method comprises the steps of:
   (i) providing a sample comprising blood or blood plasma to the device;
   (ii) reconstituting the agent;
   (iii) causing the sample to flow through the opening in the partition member;
   (iv) measuring the amount of time it takes for the formation of a clot at the opening in the porous partition member thereby stopping the flow of blood; and
   (v) correlating the time measured in step (iv) with a predetermined normal range, wherein the agent is reconstituted by providing an aqueous solution to the partition member prior to causing the sample to flow through the opening in the partition member or wherein steps (ii) and (iii) are combined and the agent is reconstituted by causing the sample to flow through the opening in the partition member.

2. A method according to claim 1, wherein the porous partition member comprises a membrane ceramic, nylon, polypropylene, polyvinylidene fluoride or fiberglass.

3. A method according to claim 1, wherein the agent capable of initiating the platelet aggregation comprises adenosine 5'-diphosphate.

4. A method according to claim 1, wherein the agent capable of initiating the blood coagulation process comprises at least one activator of the extrinsic or intrinsic pathways of prothrombin conversion.

5. A method according to claim 4, wherein the activator of the extrinsic or intrinsic pathways of prothrombin conversion comprises a thromboplastin reagent or activated cephaloplastin reagent.

6. A method of testing platelet function which comprises passing blood or platelet rich plasma through a device comprising a porous partition member, wherein the porous partition member has an opening and has dried therein at least one agent capable of activating platelet aggregation, wherein the method comprises the steps of:
   (i) providing a sample comprising blood or platelet rich plasma to the device;
   (ii) reconstituting the agent;
   (iii) causing the sample to flow through the opening in the partition member;
   (iv) measuring the amount of time it takes for the formation of a clot at the opening in the porous partition member thereby stopping the flow of blood; and
   (v) correlating the time measured in step (iv) with a predetermined normal range, wherein the agent is reconstituted by providing an aqueous solution to the partition member prior to causing the sample to flow through the opening in the partition member or wherein steps (ii) and (iii) are combined and the agent is reconstituted by causing the sample to flow through the opening in the partition member.

7. A method according to claim 1 or 6, wherein the agent is reconstituted by providing an aqueous solution to the partition member prior to causing blood or blood plasma to flow through the opening in the partition member.

8. The method of claim 1 or 6, wherein the aqueous solution is saline.

* * * * *